United States Patent [19]  [11] Patent Number: 4,950,897
Mandelis et al.  [45] Date of Patent: Aug. 21, 1990

[54] THERMAL WAVE SUB-SURFACE DEFECT IMAGING AND TOMOGRAPHY APPARATUS

[75] Inventors: Andreas Mandelis; Marek Mieszkowski, both of Toronto, Canada

[73] Assignee: University of Toronto Innovations Foundation, Toronto, Canada

[21] Appl. No.: 293,276

[22] Filed: Jan. 4, 1989

[51] Int. Cl.$^5$ ............................................. G01N 21/00
[52] U.S. Cl. .................................. 250/334; 250/338.1; 250/338.3; 250/341; 324/158 R
[58] Field of Search ............. 250/327.2 L, 334, 338.3, 250/341, 338.1; 324/158 D, 158 R, 501

[56] References Cited

U.S. PATENT DOCUMENTS

| | | | |
|---|---|---|---|
| 3,736,552 | 5/1973 | Sessler et al. | 367/7 |
| 4,218,707 | 8/1980 | Reed et al. | 358/113 |
| 4,255,971 | 3/1981 | Rosencwaig | 73/606 |
| 4,416,552 | 11/1983 | Hessemer, Jr. et al. | 374/117 |
| 4,448,525 | 5/1984 | Mikoshiba et al. | 356/73 |
| 4,459,990 | 7/1984 | Barnea | 128/656 |
| 4,468,136 | 8/1984 | Murphy et al. | 374/45 |
| 4,513,384 | 4/1985 | Rosencwaig | 364/563 |
| 4,547,892 | 10/1985 | Richey et al. | 378/8 |
| 4,578,584 | 3/1986 | Baumann et al. | 250/341 |
| 4,682,604 | 7/1987 | Fymat et al. | 128/659 |
| 4,683,750 | 8/1987 | Kino et al. | 73/606 |
| 4,694,836 | 9/1987 | Buikman et al. | 128/653 |
| 4,741,212 | 5/1988 | Rehwald | 73/600 |

OTHER PUBLICATIONS

Marek Mieszkowski, Kwan F. Leung and Andreas Mandelis, "Photopyrelectric thermal wave detection via contactless capacitive polyvinylidene fluoride (PVDF)-metal probe-tip coupling." Review of Scientific Instruments, vol. 60, No. 3 (Mar. 1989), pp. 306-316.

G. Busse, K. F. Renk, "Stereoscopic Depth Analysis by Thermal Wave Transmission for Nondestructive Evaluation", Appl. Phys. Lett, vol. 42, Feb. 15, 1983, pp. 366-368.

Gerd Busse, "Imaging With Optically Generated Thermal Waves", IEEE Transactions on Sonics and Ultrsonics, vol. SU-32, No. 2, Mar. 1985, pp. 355-364.

Primary Examiner—Constantine Hannaher
Attorney, Agent, or Firm—Spencer & Frank

[57] ABSTRACT

A thermal wave three-dimensional imaging and tomography apparatus and a thermal wave detector therefor are provided. The apparatus includes a light source for generating a laser beam which is modulated and then focussed onto one side of a solid test material. A thin pyroelectric polymer electret ($\beta$-PVDF) film having an electroded upper surface and an electrodeless lower surface supports the other side of the test material on its electroded surface. A single thin metal elongate pin or an array of thin metal elongate pins are disposed beneath the electrodeless lower surface. The pin or pins generate(s) signals upon detection of thermal waves passing through the solid test material resulting from the laser excitation due to the photopyroelectric ($P^2E$) effect. Since the pins are small, the signals generated by the pins represent local thermal wave progagation through the test material. The laser beam and the test material are moved relative to one another so that the laser beam scans substantially the entire one side of the test material. When using a single pin, the pin is moved with respect to the other side of the test material so that the pin scans the other side of the film to detect local thermal wave propagation through the test material during the entire scan of the laser beam on the test material. When using an array of pins, the array of pins remains stationary with respect to the other side of the material during the scan of the laser beam on the test material. The resulting signals generated by the pins during the laser beam scan are conveyed to a microcomputer via signal conditioning circuitry wherein a three-dimensional image of the test material subsurface structure is formed.

22 Claims, 7 Drawing Sheets

SCANNED COORDINATES (mm)

THERMAL WAVE SUB-SURFACE DEFECT IMAGING AND TOMOGRAPHY APPARATUS

The present invention relates to imaging and in particular to a thermal wave subsurface imaging and tomography apparatus and a thermal wave detector therefor.

Thermal wave detection and imaging is known in the art and has been contemplated for use in the nondestructive testing of solid materials. Presently, arrangements include a light source for irradiating locally, a solid material with a thin modulated laser beam thereby causing local thermal wave propagation in the solid material. A detector having an electroded upper surface and an electroded lower surface supports the solid material being scanned on its electroded upper surface. The detector generates an integrated response signal proportional to the temperature change in the detector resulting from the local thermal waves passing through the material. The integrated response signal consists of weighted contributions of the thermal wave propagation from many locations in the excited material. Generally, since the electrode surfaces are large, the integrated response signal is an average value of the probed temperature field over a large area of the test material. This, of course, reduces lateral resolution when analyzing the response signal to form an image of the scanned test material.

Other problems exist when using these arrangements in that the thermal wave information generated by the detector allows only a two-dimensional image of the scanned material to be formed. This is due to the fact that the integrated signal formed by the detector does not include any phase interference information of the thermal waves propagating through neighboring regions of the solid material. Accordingly, there is a need for improved thermal wave imaging and tomography apparatus.

It is therefore an object of the present invention to obviate or mitigate the above disadvantages.

According to the present invention there is provided a thermal wave detector comprising:

a pyroelectric electret film having an electrode disposed on one side thereof, said electrode for supporting solid material; and conductive detection means disposed on the other side of said film and being spaced from said electrode, said detection means being capacitively or thermally coupled to said film upon propagation of thermal waves through said solid material.

In another aspect of the present invention there is provided a thermal wave imaging apparatus comprising:

a source for generating a narrow beam of radiation to be scanned substantially over one side of solid material;

a pyroelectric electret film having an electrode disposed on one side thereof, said electrode for supporting the other side of said material;

at least one conductive detector disposed on the other side of said film and being spaced from said electrode, said detector being capacitively or thermally coupled to said film upon propagation of thermal waves through said material and generating output signals upon detection of said thermal waves;

means for scanning the other side of said film with said detector to detect locally said thermal wave propagation substantially throughout said material over the scan of said radiation; and processing means receiving said output signals and generating therefrom a three-dimensional image of said material.

Preferably, the conductive detector comprises a thin metal elongate pin having its in contact with or positioned in close proximity to the other side of the pyroelectric film (i.e. between 0.0 mm and 2.0 mm). It is also preferred that the pyroelectric film is a commercially available beta-phase polyvinylidene fluoride ($\beta$-PVDF) type film having only one electroded surface.

Preferably the conductive detector includes a planar array of metal pins or a metal dot array on the PVDF film in contact with a Charge Coupled device (CCD), each of which detects locally the propagating thermal waves passing through the material as the radiation is scanned along the one side of the material. This removes the need to move the pins with respect to the other side of the film and constitutes a faster means for scanning the other side of said film to detect thermal wave propagation.

The present device provides advantages in that the thermal waves can be detected locally using a simple detector thereby allowing three-dimensional imaging of solid material using the photopyroelectric ($P^2E$) effect. Furthermore, by using planar arrays of thin metal pins, or PVDF-CCD detection the entire sub-surface structure of the solid material can be scanned without requiring movement of the detectors with respect to the film. Also, by providing the planar array of pins, the thermal wave information can be accessed faster thereby increasing the imaging speed of the apparatus.

Embodiments of the present invention will now be described by way of an example only with reference to the accompanying drawings in which:

FIG. 1b is an enlarged perspective view of a portion of the apparatus shown in FIG. 1a;

Figure 1A:
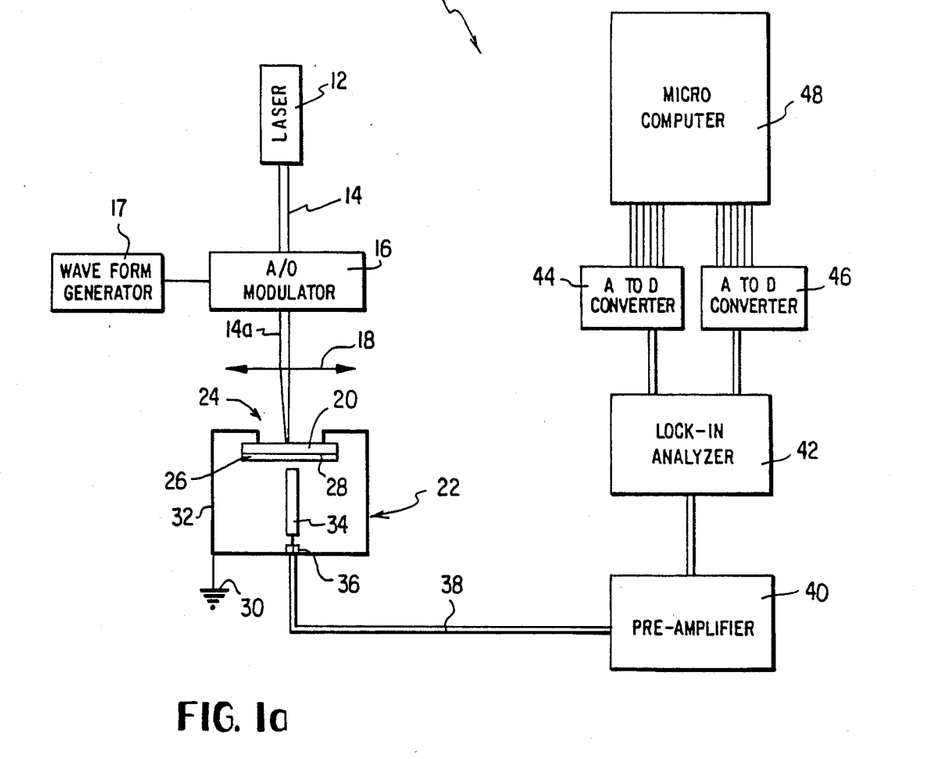
FIG. 1a is a side view of wave imaging and tomography apparatus.
Figure 1B:
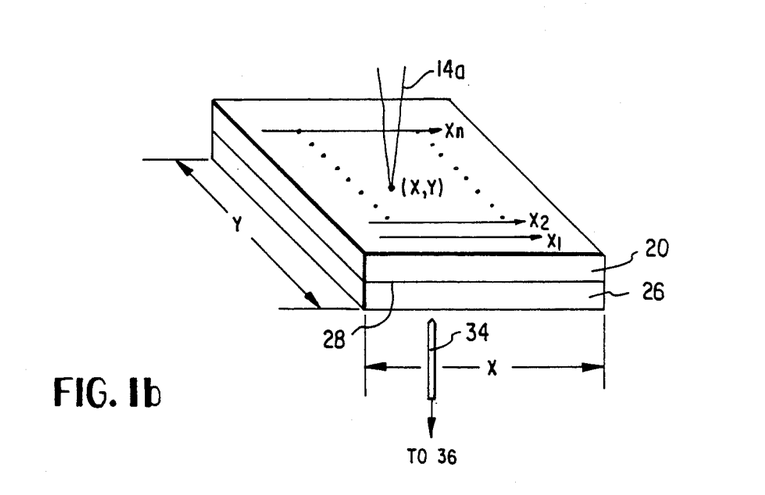
Figure 2:
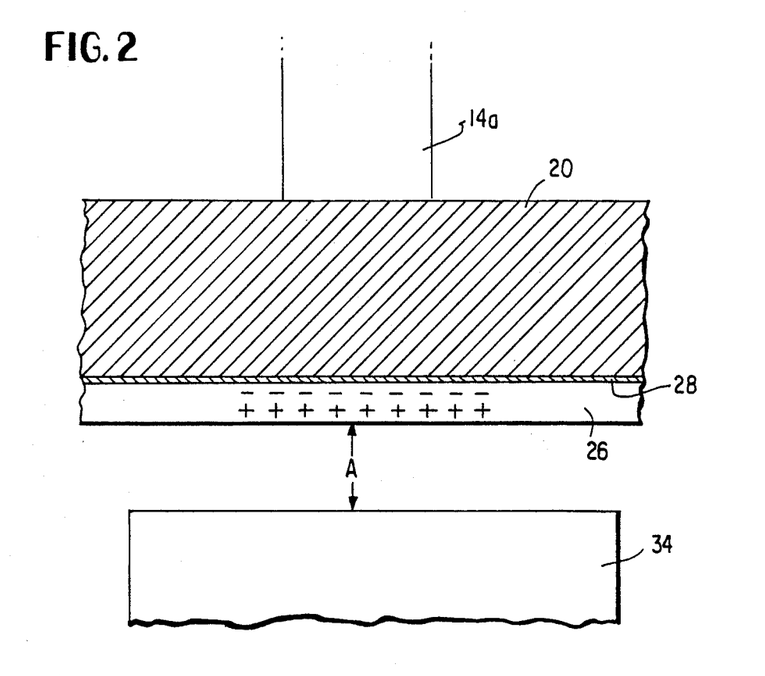
FIG. 2 is an enlarged side view of the portion of the apparatus illustrated in FIG. 1b.

Referring to FIGS. 1a, 1b and 2, a thermal wave tomography apparatus is shown and generally indicated by reference numeral 10. The apparatus includes a radiation source, preferably a laser 12 generating a laser beam 14 having a thin beam waist. An Acousto-Optic (A/O) modulator 16 modulates the laser beam 14 at a pre-determined frequency and is driven by a waveform generator 17. The modulated laser beam 14a passes through a lens 18 and is focussed onto the surface of a test sample 20 formed from solid material.

A radio-frequency (RF) shielding metal cage 22 is disposed below the laser 12 and includes a housing 24. The housing 24 supports a thin beta-phase polyvinylidene fluoride ($\beta$-PVDF) pyroelectric electret film 26 having a thickness preferably between 9 to 50 $\mu$m. The pyroelectric film 26 has an electrode 28 covering its upper surface that is connected to a ground 30 via a highly conductive connection 32. The electrode 28 supports the test sample 20 so that substantially the entire lower surface of the test sample is in contact with the electrode 28 and so that the test sample 20 lies in the path of the light beam 14a. A thin layer (not shown) of a thermal compound of the type such as for example, Wakefield #120-8 may be disposed between the sample 20 and the electrode 28 to improve the thermal contact between the test sample and the electrode. The laser 12 and the cage 22 are moveable with respect to one another so that substantially the entire upper surface of the test material 20 can be scanned with the modulated laser beam 14a.

The bottom surface of the film 26 is free from an electrode. A thin elongate metal pin 34 formed from brass and having a small tip diameter is disposed below the lower surface of the film 26. The pin 34 is movable along X and Y axes so that substantially the entire lower surface of the film 26 can be scanned by the pin. The pin 34 can also be moved vertically with respect to the film 26 along the Z axis so that the distance A between the tip of the pin and the lower surface of the film 26 can be varied. However, it is desired to maintain the distance A between 0.0 mm and 2.0 mm.

The other end of the pin 34 is connected to a BNC connector 36 which shields the pin 34 and rejects RF signals. A 50 Ohm coaxial cable 38 such as that sold under the name MICRODOT (trademark) is coupled to the BNC connector 36 at one end and to a pre-amplifier/bandpass filter 40 at the other end. The output of the pre-amplifier/bandpass filter 40 is applied to a lock-in analyzer 42. Analog to digital (A to D) converters 44 and 46 respectively, each receive one of the output signals of the analyzer 42, these being an in-phase signal and a quadrature signal. The A to D converter 44 receives the In-Phase signal while the A to D converter 46 receives the quadrature signal. The digital output signals of the A to D converters 44 and 46 are applied to a micro-computer 48 for processing using Fast Fourier Transforms (FFT's) adapted to thermal wave physics to generate a three-dimensional image of the test sample 20.

In operation, when the test sample 20 is irradiated at a point (x,y) on its surface with the focussed and modulated laser beam 14a, a spatially well defined thermal wave is generated and propagates through the test sample 20. The thermal wave field passes through the test sample 20 and generates a temperature field T(x,y,z,t) in the film 26 since the electrode 28 is in contact with the lower surface of the sample 20. The temperature field T(x,y,z,t) which propagates in the film 26 can be expressed as:

$$T(x,y,z,t) = T_{AC}(x,y,z)exp(j[\omega t + \psi(x,y,z)]) + T_{DC}(x,y,z) + T_0 \quad (1)$$

where $T_o$ is the ambient temperature; $T_{AC}(x,y,z)$ is the amplitude of the AC component of the temperature field in the pyroelectric film 26; $\psi(x,y,z)$ is the phase of the AC component of the temperature field; and $T_{DC}(x,y,z)$ is the magnitude of the DC component of temperature field in the pyroelectric film 26 for a given configuration and angular frequency $\omega$ of laser radiation 14a.

A potential difference is developed in the film 26 between its upper and lower surfaces due to charge displacement in the polymer matrix of the film 26 which is proportional to the local temperature increase in the film 26 induced by the thermal wave propagation through the test sample 20. Under this photothermal excitation, the pyroelectric potential difference U(x,y,t) induced in the film 26 between the upper and lower surfaces of the film is given by:

$$U(x,y,t) = \frac{p \cdot L_{PVDF}}{\epsilon} <T(x,y,z,t)>_z \quad (2)$$

where p is the PVDF pyroelectric coefficient which is equal to $(30 \times 10^{-6} C/m^2 K)$, $L_{PVDF}$ is the film thickness, $\epsilon$ is the dielectric constant of the film 26 and $<T(x,y,z,t)>_z$ is the spatially averaged temperature field in the vertical axis z of the pyroelectric film 26. The spatially averaged temperature field $<T(x,y,z,t)>_z$ in the film 26 is defined as:

$$<T(x,y,z,t)>_z = \frac{1}{L_{PVDF}} \int_0^{L_{PVDF}} T(x,y,z,t)dz \quad (3)$$

Equation 2 is valid only for one-dimensional temperature distribution when T(x,y,z) is sampled locally at x,y coordinates, or in the case when the electrode 28 is infinitesimally small. Typically, a conventional PVDF film with a metal electrode on each side forms a capacitor which acts as an integrating detector. Thus, with the pin 34 disposed beneath and spaced from the film 26, the tip of the pin and the electrode 28 function similar to a parallel plate capacitor with unequal plate areas. However, the capacitor does not function as an integrator over the surface of the sample 20 as do conventional detectors but rather as a local detector examining a small portion of the sample 20. Accordingly, the voltage $<U(x,y)>_{x,y}$ developed between the pin 34 and the electrode 28 can be expressed as:

$$<U>_{x,y} = \frac{1}{a^2} \int_{a/2}^{a/2} \int_{a/2}^{a/2} U(x + x', y + y')dx'dy' \quad (4)$$

wherein a is the length of the tip of the pin 34. Using equations 2 to 4, the AC voltage $U_{AC}(x,y,z,t)$ developed between the pin 34 and the electrode 28 at position (x,y) on the film 26 can be expressed as:

$$U_{AC}(x,y,z,t) = \frac{p}{\epsilon a^2} \int_{a/2}^{a/2} \int_{a/2}^{a/2} \int_0^{L_{PVDF}} T_{AC}(x + x', y + y', z)sin[\omega t + \psi(x + x', y + y', z)]dzdx'dy'. \quad (5)$$

Accordingly, the displacement current $I_D(t)$ through the PVDF film 26 is then given by:

$$I_D(t) = A \cdot \frac{d<P(t)>_z}{dt} \quad (6)$$

where A is the surface area of the electrode 28, and $$<P(t)>_z = \frac{1}{L_{PVDF}} \int_0^{L_{PVDF}} P(z,t)dz \quad (7)$$

is a spatially averaged dipole moment $<P(t)>_z$ per unit volume of the film 26 over the vertical dimension z. The oscillating dipole moment $<P(t)>_z$ that is responsible for the displacement current $I_D$ sets up an electric field which penetrates the distance A between the PVDF film 26 and the metal pin 34. Thus, the metal pin 34 can pick up the electric field without touching the film and hence, generates a voltage proportional to the local temperature field in the film 26. This permits a purely contactless detection technique for the photopyroelectric effect. When the pin 34 is in contact with the film 26, the thermal field between the front surface of the film and the back surface at the pin causes a voltage to be generated in the pin 34 which is also proportional to the local temperature field in the film 26.

The voltage generated in the pin 34 is conveyed to the co-axial cable 38 via the BNC connector 36. The co-axial cable 38 conveys the signal to preamplifier 40 which cleans and amplifies the signal. The lock-in analyzer 42 and A to D converters 44 and 46 condition the signal prior to it being applied to the micro-computer 48. The lock-in amplifier 42 receives the output of the pre-amplifier 40 and rejects all stray signals other than those received that have the same frequency as the frequency of the modulated excitation beam 14a. This results in a highly enhanced signal-to-noise ratio with respect to signals that are directly traceable to the excitation beam 14a. The demodulated outputs of the lock-in analyzer which are a dc in-phase component and an out-of-phase (quadrature) component are, as mentioned above, conveyed to the micro-computer 48 via A to D converters 44 and 46 respectively.

When forming a three-dimensional image of the test material 20 using a single pin, the laser beam 14a is scanned across the entire upper surface of the material in successive passes illustrated in FIG. 1a as $x_1, x_2, \ldots x_n$. For various points m along each pass $x_n$, the pin 34 is moved incrementally beneath the film 26 in the direction of the laser beam pass until the pin 34 has scanned the film 26 beneath the pass for the number of points m along the scan line. The signals generated by the pin 34 at each point for each scan line of the laser beam 14a are conditioned and stored in the micro-computer 48.

By scanning the entire surface of the test sample 20 with the laser beam 14a and by detecting the thermal waves as they propagate through the sample 20 in this manner, signals representing the sub-surface structure at a given depth Z of the sample are generated by the pin 34. The signals received by the computer 48 are then processed using FFT's adapted to thermal wave physics to form a two-dimensional image of the test sample 20.

By scanning the material 20 at n intervals with the laser beam 14a and at m intervals for each laser beam scan $x_n$ with the detector pin 34, an n×m dimensional matrix of thermal wave tomographic information can be generated for each scan line $x_n$ at a given depth Z. Each measurement taken along the scan lines will correspond to a particular spatial thermal wave frequency measured in $cm^{-1}$. Using a modified Tomographic algorithm such as Convolution, Backprojection, Fourier Space Inversion, Arithmetic Reconstruction Technique, Diffraction Methods (for example Born Approximation) and an FFT inversion, the spatial thermal wave information can be converted into units of cm thereby forming the required 2-D image. Thus, the 2-D array of information will give a two dimensional image corresponding to a specific slice of the material at a fixed depth. The depth will be determined using the phase information of the signals generated by the pin 34. Accordingly, a three dimensional matrix of thermal wave information can be formed by completing a plurality of scan lines $x_i$ across the material 20 in the y direction and thus, generating j slices which when inverted form the 3-D image of the scanned volume including sub-surface defects.

By repeating the scan lines $x_n$ using different modulation frequencies, 3-D imaging contrast may be enhanced for sub-surface structures lying at particular depths below the surface of the sample. Since defects in the material affect the propagation of the thermal waves, formation of a 3-D image using the thermal waves will pin-point defects in the sub-surface structure of the sample 20.

Figure 3:
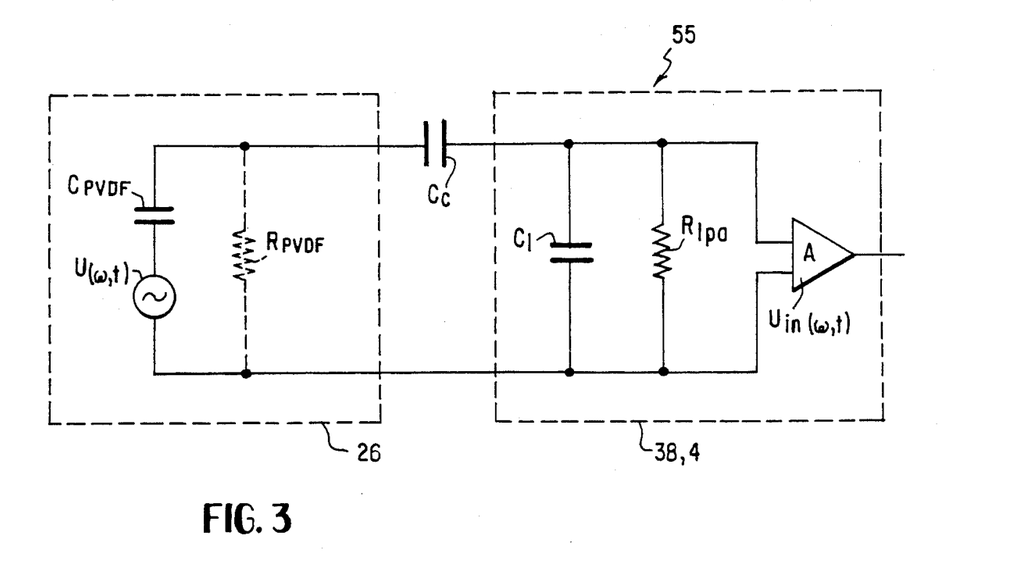
FIG. 3 is a diagram of an electronic circuit equivalent of a portion of the device illustrated in FIG. 1.

Referring to FIG. 3, an electronic equivalent circuit diagram representing the film 26, the pin 34, the cable 38 and the pre-amplifier 40 is shown and is generally indicated by reference numeral 55. The circuit diagram was derived based on a modulation frequency for the laser beam 14a between 0.5 Hz and 100 Hz. Since the internal resistance of the film 26 is large compared to the parallel impedance of the capacitor defined by the pin 34 and electrode 28, the resistance of the film 26 was ignored. Thus, the capacitance $C_{PVDF}$ of the film 26 and the capacitance $C_C$ between the film 26 and the pin 34 represent the impedance of the film 26. $C_f$ represents the capacitance of the co-axial cable 38 combined with the capacitance of the pre-amplifier 40. $U(\omega,t)$ represents the input excitation of the modulated laser beam 14a whilst $R_{1pa}$ represents the internal resistance of the pre-amplifier 40 and the co-axial cable 38.

Figure 4A:
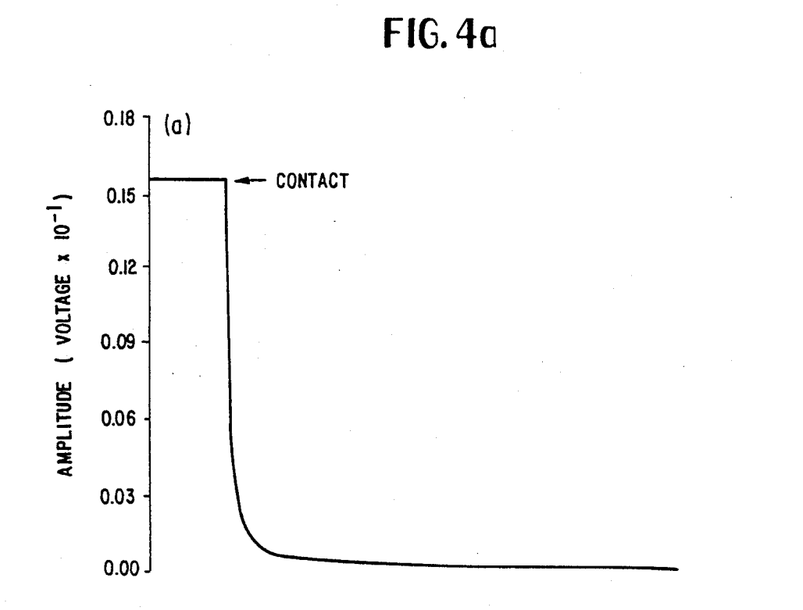
FIGS. 4a and 4b are graphs illustrating the theoretical response of the circuit illustrated in FIG. 3 with respect to one parameter.
Figure 4B:
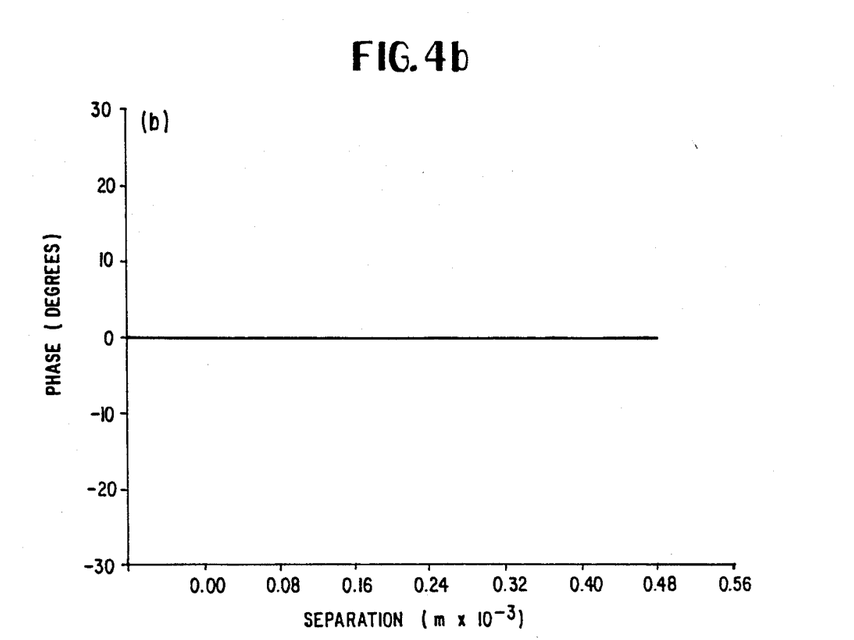

Using this model, responses were analyzed to predict theoretically, the operation of the apparatus shown in FIG. 1. Referring to FIGS. 4a and 4b, the voltage amplitude and phase response of the theoretical circuit as a function of the separation distance A of the tip of the pin 34 from the film 26 are shown. As can be seen, the model predicts that the signal induced in the pin 34 due to the capacitive or thermal coupling between the pin 34 and the film 26 decreases rapidly as the pin is moved away from the lower surface of the film. Also, resolution is increased as the pin 34 is moved towards the film 26. However, it should be noted that the phase of the signal induced in the pin is predicted to remain constant.

Figure 5A:
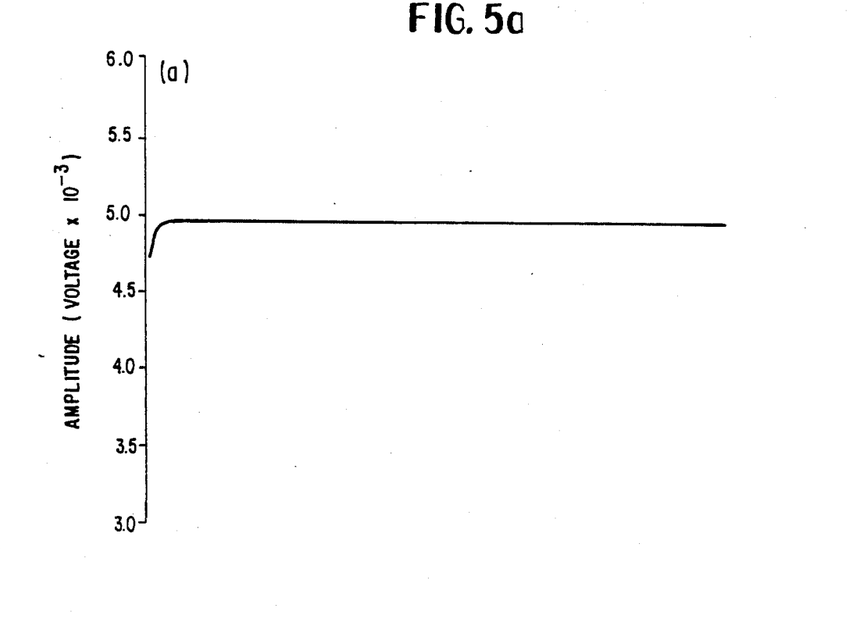
FIGS. 5a and 5b are graphs illustrating the theoretical response of the circuit illustrated in FIG. 3 with respect to another parameter.
Figure 5B:
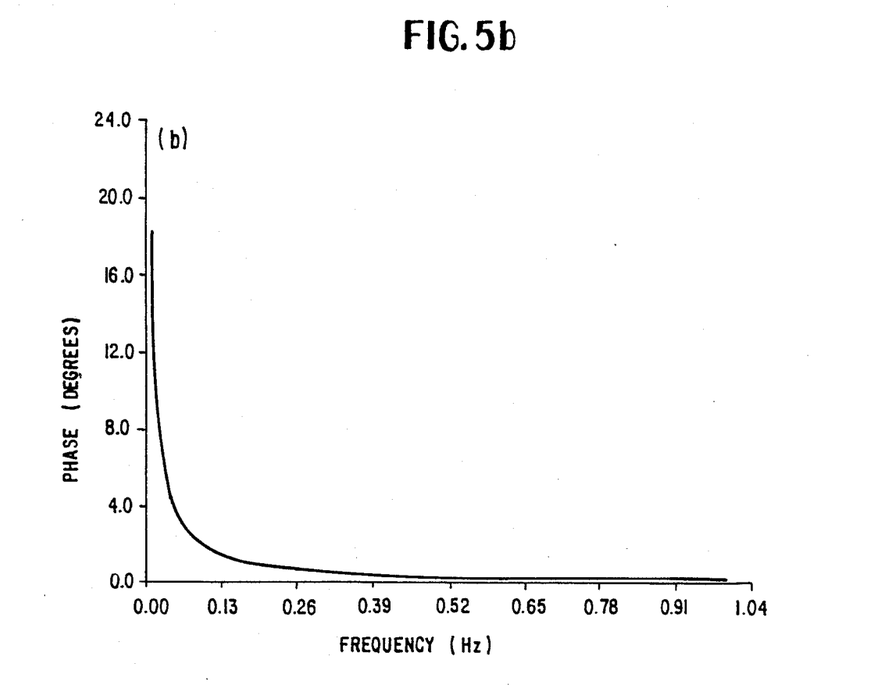

FIGS. 5a and 5b show the voltage amplitude and phase response of the theoretical circuit 55 for various laser beam 14a modulation frequencies when the pin 34 is in contact with the lower surface of the film 26. As can be seen, the circuit predicts that little amplitude and phase distortion will occur in the signal generated in the pin at modulation frequencies between 0.5 Hz and 100 Hz. The equivalent circuit also predicts that the voltage amplitude and the phase of the signal will be distorted at frequencies below 0.1 Hz. However, since the frequency range of interest is usually between 0.5 Hz and 100 Hz, the model predicts that the device shown in FIG. 1 will provide a flat voltage amplitude and phase response in this range.

The system shown in FIG. 1 was used to scan the surface of a copper strip. A 10 mW He-Ne laser manufactured by Hughes Aircraft Company under model number 3235H-PC was used to generate the laser beam 14 having a beam waist of 0.1 mm. An ISOMET 1201E-2 A/O modulator driven by a Hewlett Packard 3312A waveform generator received the laser beam 14 and performed the necessary modulation. The modulated and focussed laser radiation was scanned on the surface of the copper strip by moving the RF shielding cage 22 including the sample 20 and pin 34 via a translation stage with a precision of delta (X) ($\Delta(x)$) equal to 0.02 mm.

Figure 6A:
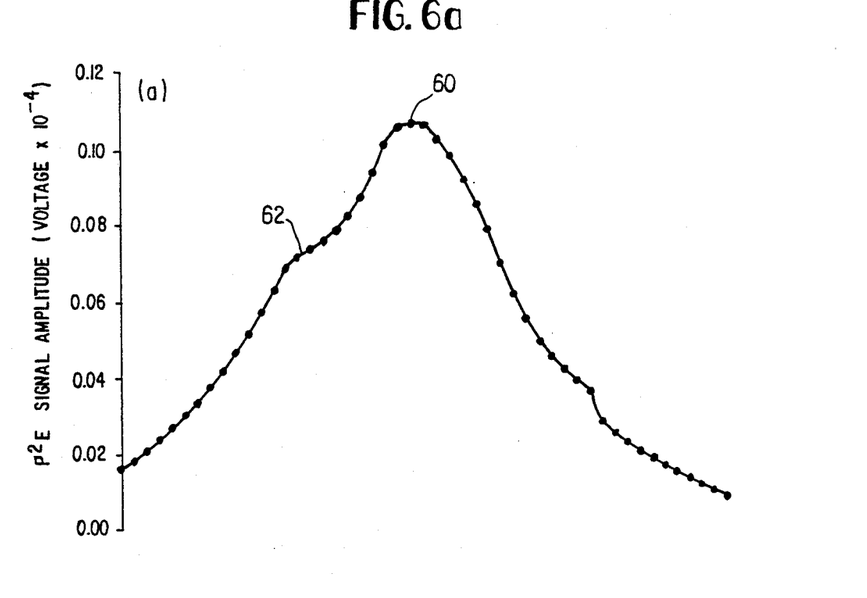
FIGS. 6a and 6b are graphs illustrating the experimental response of the apparatus shown in FIG. 1 in one condition.
Figure 6B:
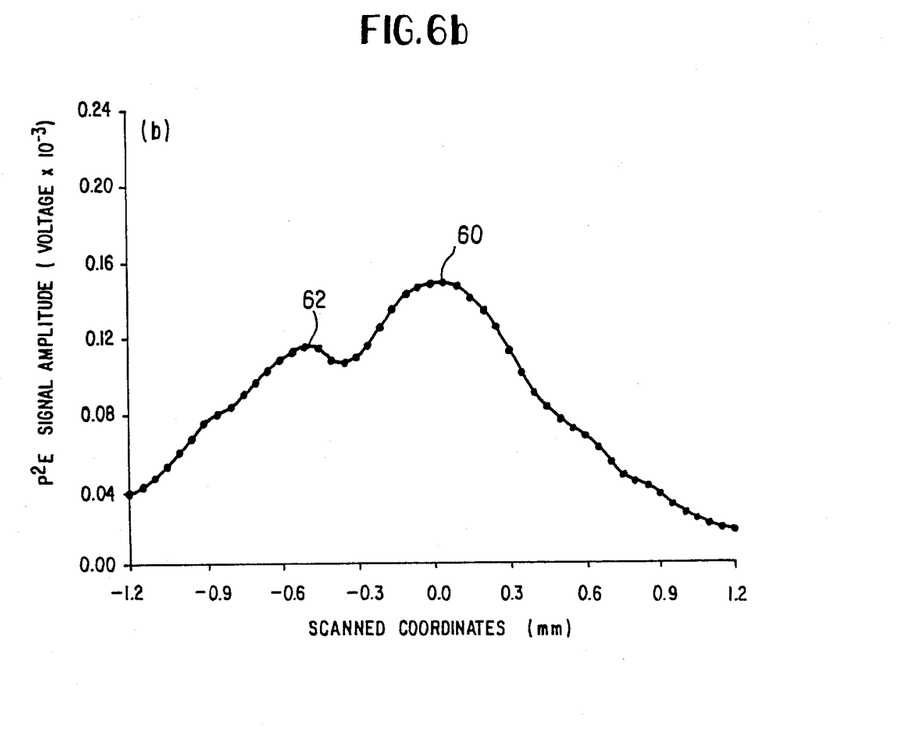

FIGS. 6a and 6b show the output of the pin 34 when scanning the copper strip with a 100 Hz modulated laser beam 14a for a single one dimensional scan $x_n$ of the laser beam 14a on the copper strip with the pin 34 in contact with the lower surface of the film 26 and with the pin 34 spaced from the lower surface of the film 26 respectively. The broad maxima 60 shown in the two graphs corresponds to the point where the laser beam 14a was located directly above the pin 34. The maximum 62 to the left of the broad maxima 60 may be attributed to thermal wave distribution in the film 26 and passage through a thermally inhomogeneous part of the strip.

Figure 7A:
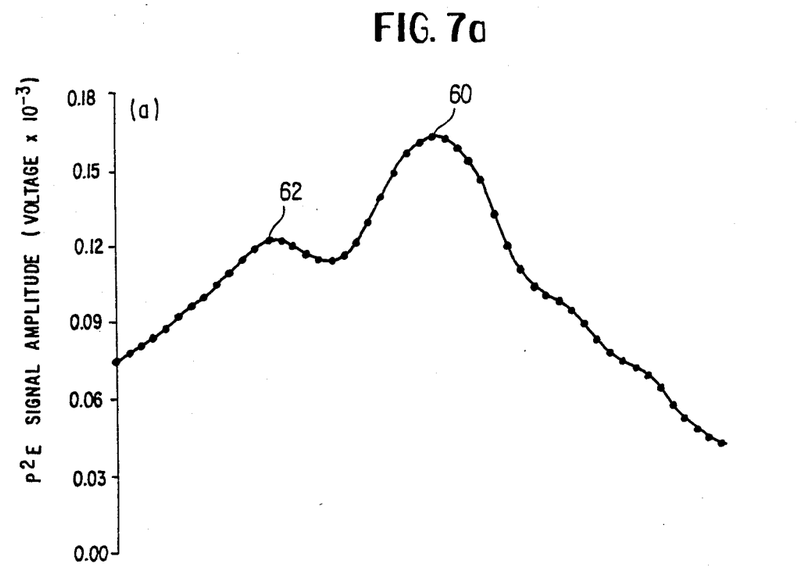
FIGS. 7a and 7b are graphs illustrating the experimental response of the apparatus shown in FIG. 1 in another condition.
Figure 7B:
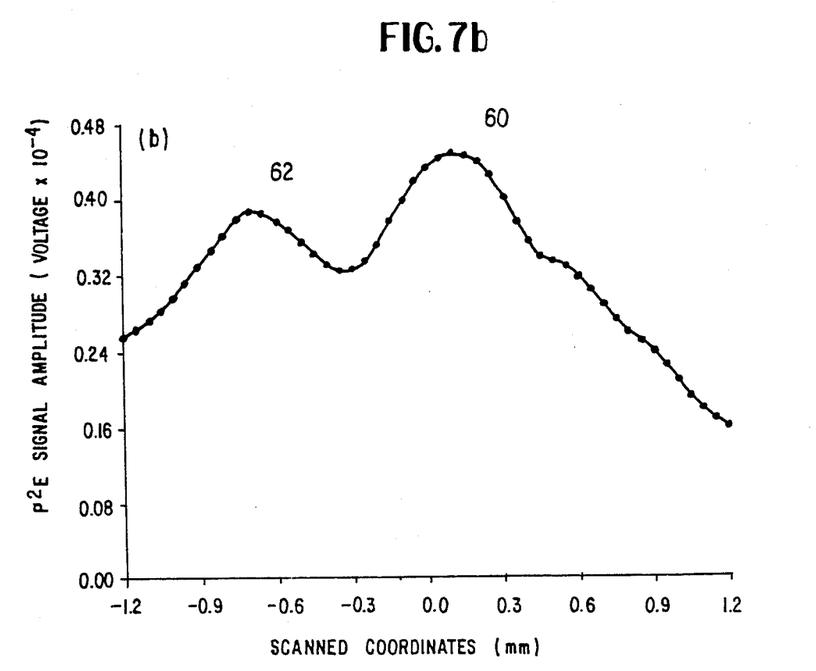

FIGS. 7a and 7b are similar to FIG. 6a and 6b. However, the modulation frequency for the laser beam 14a was chosen to be 10 Hz. As can be seen, the shoulder 62 on the left-hand side of the broad maxima 60 is more pronounced using the 10 Hz modulation frequency as compared with the 100 Hz modulation frequency. The separation of the shoulder 62 from the maximum 60 is greater at the 10 Hz modulation frequency which suggests that the shoulder 62 represents a sub-surface defect in the copper strip that is positioned to the left of the impingement point of the laser beam 14a on the copper strip.

Figure 8A:
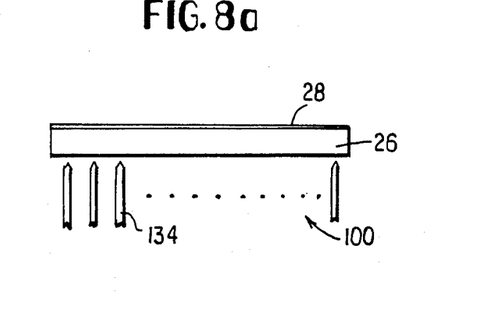
FIGS. 8a and 8b are side and perspective views respectively of another embodiment of a portion of the apparatus illustrated in FIG. 1.
Figure 8B:
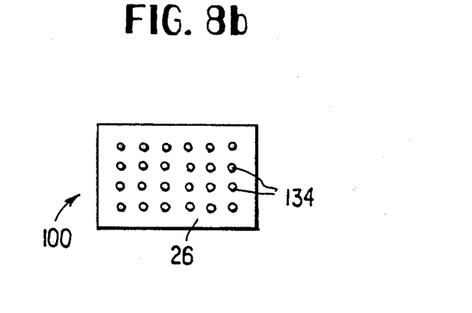

Referring now to FIGS. 8a and 8b, another embodiment of the thermal wave detector is shown. As can be seen, rather than using a single metal pin 34 and scanning the lower surface of the film 26 with the pin 34 for each scan of the laser beam, an array 100 of pins 34 is provided beneath the lower surface of the film 26. The array is positioned so that the rows of pins are parallel to and are disposed directly beneath the scan lines $x_n$ of the laser beam 14a. This allows substantially the entire lower surface of the film 26 to be scanned without moving the pins 134. This is achieved by examining separately the output of each pin 134 in the row beneath the laser radiation scan line for each one dimensional scan $x_n$ of the laser beam 14a. Accordingly, the laser beam 14 need only scan a region once as opposed to multiple scans along each scan line which are required for tomography when using a single pin 34.

The other end of each of the pins 134 is connected to a suitable port which allows the information generated by each pin to be sampled and stored by the micro-computer 48 after it has been conditioned by the appropriate circuitry. The microcomputer 48 which receives all of the thermal wave tomographic information from each of the pins 134 is then able to form a three-dimensional image of the sample 20. By adjusting the modulation frequency of the laser radiation, an optimal contrast image of the sample with respect to sub-surface structure can be formed in the same manner previously described. Thus, this embodiment removes the need for moving the pins 34 with respect to the lower surface of the film 26 in order to detect thermal wave propagation in the sample 20 for each laser scan.

FIGS. 9a, 9b, 10a and 10b show other embodiments of the thermal wave detector wherein the array 200 includes only a single row of pins 234 and is designed to conform with the shape of the sample 20 to be irradiated. When using this type of array 200, the array needs only to be moved in a single direction Z so that the pins 234 are aligned with the successive one dimensional scans $x_n$ of the laser beam 14a on the sample 20. Similarly, the output of the array of pins is conveyed to a suitable port which allows the information generated by the pins 234 to be sampled and conditioned prior to being processed and stored in the microcomputer 48.

Figure 9A:
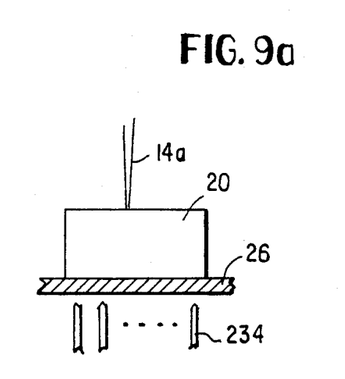
FIGS. 9a and 9b are top plan and perspective views respectively of another embodiment of the portion illustrated in FIGS. 8a and 8b.
Figure 9B:
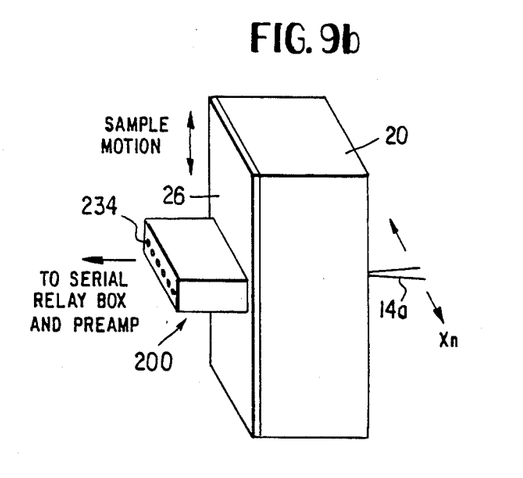
Figure 10A:
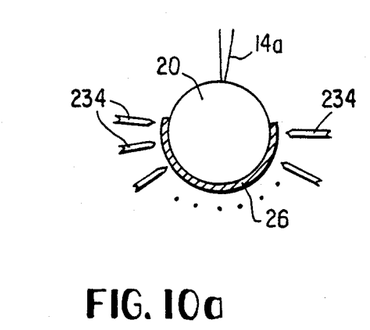
FIGS. 10a and 10b are top plan and perspective views respectively of still yet another embodiment of the portion illustrated in FIGS. 8a and 8b.
Figure 10B:
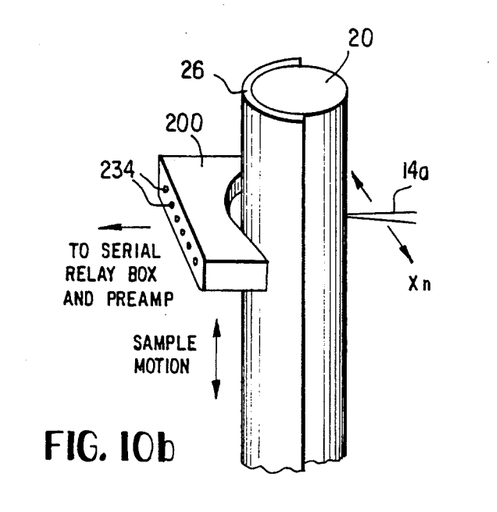

As opposed to using metal pins as illustrated in the embodiments of FIGS. 8 to 10, a PVDF film having its unelectroded surface metallized with small (1 $\mu$m) dots in contact with a charge coupled device (CCD) or inside a metallic cage such as that shown in FIG. 1a having a pin hole provided in the top can be used to detect thermal wave propagation throughout the sample. The signals generated by the CCD or the metallic cage upon detection of thermal wave propagation throughout the sample are conveyed to the micro-computer in the manner previously described to allow a 3-D image of the sample to be formed.

Although the present invention is shown using a co-axial cable 38 coupled to the pin 34 and the preamplifier 40, the co-axial cable can be removed and replaced with a FET amplifier coupled directly to the pin or pins. This removes the large capacitance associated with the cable 38 and hence, increases the magnitude of the output signal received at the input terminals of the pre-amplifier 40. Furthermore, the A/O modulator can be replaced with a mechanical chopper for performing the necessary laser beam modulation.

It should also be realized that the look-in analyzer may be removed and replaced using fast A to D convertors, digital filtering and a fast micro-computer. This allows the sampled information to be processed in the digital domain.

We claim:

1. A thermal wave detector comprising:
   a pyroelectric electret film having an electrode disposed on one side thereof, said electrode for supporting a solid material; and
   conductive detection means disposed on the other side of said film and being spaced from said electrode, said detection means being capacitively or thermally coupled to said film upon propagation of thermal waves through said material.

2. The detector as defined in claim 1 wherein said conductive detection means is in the form of a thin elongate metal pin.

3. The detector as defined in claim 2 wherein the tip of said thin elongate metal pin is spaced from said other side at a distance of not more than 2.0 mm.

4. The detector as defined in claim 3 wherein said metal pin is formed from brass.

5. The detector as defined in claim 1 wherein said pyroelectric electret film is formed from beta phase polyvinylidene fluoride.

6. The detector as defined in claim 1 wherein said conductive detection means is in the form of a plurality of spaced detectors disposed beneath said other side.

7. The detector as defined in claim 6 wherein each of said spaced detectors in said array is in the form of a thin elongate metal pin.

8. The detector as defined in claim 7 wherein each of said thin elongate metal pins is spaced from said other side at a distance of not more than 2.0 mm.

9. The detector as defined in claim 6 wherein said spaced detectors are in the form of dots formed on the other side of said film, said dots being in communication with a charge coupled device or a metallic cage with a pin hole provided in the top thereof.

10. The detector as defined in claim 1 wherein said pyroelectric electret film conforms with the shape of said solid material.

11. A thermal wave imaging apparatus comprising:
   a source generating a narrow beam of radiation to be scanned across a test sample of solid material;
   a pyroelectric electret film detector having an electrode disposed on one side thereof, said electrode for supporting said test sample in the path of said radiation;
   at least one conductive detector disposed on the other side of said film and being spaced from said electrode, said detector being capacitively or thermally coupled to said film upon propagation of thermal waves through said test sample and generating output signals upon detection of said thermal waves;
   means for scanning the other side of said film with said detectors to detect said thermal waves over said entire test sample; and
   processing means receiving said output signals and generating therefrom a three-dimensional image of said test sample.

12. The thermal wave imaging apparatus as defined in claim 11 wherein said conductive detector is in the form of a thin elongate metal pin.

13. The thermal wave imaging apparatus as defined in claim 12 wherein the tip of said thin elongate metal pin is spaced from said other side by a distance of not more than 2.0 mm.

14. The thermal wave imaging apparatus as defined in claim 11 wherein said metal pin is formed from brass.

15. The thermal wave imaging apparatus as defined in claim 14 wherein the other end of said metal pin is connected to a co-axial cable, said co-axial cable also being connected to said processing means.

16. The thermal wave imaging apparatus as defined in claim 11 wherein said pyroelectric film is formed from polyvinylidene fluoride.

17. The thermal wave imaging apparatus as defined in claim 11 further comprising an array of spaced conductive detectors disposed beneath said other side.

18. The thermal wave imaging apparatus as defined in claim 17 wherein each of said conductive detectors in said array is in the form of a thin elongate metal pin.

19. The thermal wave imaging apparatus as defined in claim 17 wherein each of said conductive detectors is in the form of a metallized dot formed on the other side of said film, said dots being in communication with a charge coupled device or a metallic cage having a pin hole formed in the top thereof.

20. The thermal wave imaging apparatus as defined in claim 11 wherein said pyroelectric electret film conforms with the shape of said test sample.

21. The thermal wave imaging apparatus as defined in claim 11 wherein said processing means includes a preamplifier/bandpass filter and a microcomputer.

22. The thermal wave imaging apparatus as defined in claim 21 wherein said microcomputer processes said output signals using Fast Fourier Transforms adapted to thermal wave physics to generate said three-dimensional tomographic image.

* * * * *